United States Patent
Mohanty et al.

(10) Patent No.: US 10,241,078 B2
(45) Date of Patent: Mar. 26, 2019

(54) FUNCTIONALIZED NANOTUBE SENSORS AND RELATED METHODS

(71) Applicant: University of Utah Research Foundation, Salt Lake City, UT (US)

(72) Inventors: Swomitra Kumar Mohanty, Salt Lake City, UT (US); Manoranjan Misra, Salt Lake City, UT (US); Younghwan Kim, Salt Lake City, UT (US); Jules Magda, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 661 days.

(21) Appl. No.: 14/439,153

(22) PCT Filed: Oct. 29, 2013

(86) PCT No.: PCT/US2013/067319
§ 371 (c)(1),
(2) Date: Apr. 28, 2015

(87) PCT Pub. No.: WO2014/070780
PCT Pub. Date: May 8, 2014

(65) Prior Publication Data
US 2015/0293057 A1 Oct. 15, 2015

Related U.S. Application Data

(60) Provisional application No. 61/861,107, filed on Aug. 1, 2013, provisional application No. 61/795,850, filed on Oct. 29, 2012.

(51) Int. Cl.
*G01N 27/49* (2006.01)
*G01N 33/497* (2006.01)
*G01N 33/551* (2006.01)

(52) U.S. Cl.
CPC .......... *G01N 27/49* (2013.01); *G01N 33/551* (2013.01); *G01N 33/497* (2013.01); *G01N 2033/4975* (2013.01); *G01N 2333/35* (2013.01)

(58) Field of Classification Search
CPC .... G01N 27/49; G01N 33/497; G01N 33/551; G01N 2033/35; G01N 2033/4975
See application file for complete search history.

(56) References Cited

U.S. PATENT DOCUMENTS

2007/0153267 A1   7/2007   Wang et al.
2008/0305489 A1   12/2008   Thomas et al.
(Continued)

FOREIGN PATENT DOCUMENTS

WO   WO 2006/083269   8/2006
WO   WO 2009/045116   4/2009
(Continued)

OTHER PUBLICATIONS

Gao, Chao, et al. "Multihydroxy polymer-functionalized carbon nanotubes: synthesis, derivatization, and metal loading." Macromolecules 38.21 (2005): 8634-8648.*
(Continued)

*Primary Examiner* — Robert J Eom
(74) *Attorney, Agent, or Firm* — Thorpe North & Western, LLP

(57) ABSTRACT

Functionalized nanotube arrays, sensors, and related methods of detecting target compounds are presented. A functionalized nanotube array (235) can include a plurality of metal oxide nanotubes (240). The metal oxide nanotubes (240) can be formed of a metal oxide and can have an interior or exterior surface that is optionally functionalized with at least one metal ion. These metal nanotubes (240) can be used in a sensor (200) for detecting target compounds
(Continued)

such as volatile organic compounds, and biomarkers in a fluid environment. The sensor (200) can further include a power source (245) configured to apply a voltage to the nanotube array (235) and a current sensor (250) configured to monitor and detect changes in a response current which varies upon binding with the target compounds.

20 Claims, 7 Drawing Sheets

(56) References Cited

U.S. PATENT DOCUMENTS

| | | | |
|---|---|---|---|
| 2009/0275143 A1* | 11/2009 | Misra | G01N 27/127 |
| | | | 436/130 |
| 2011/0045523 A1 | 2/2011 | Strano et al. | |
| 2012/0178187 A1 | 7/2012 | Radtkey et al. | |
| 2012/0293802 A1 | 11/2012 | Ozin et al. | |
| 2013/0128265 A1 | 5/2013 | Zhao et al. | |

FOREIGN PATENT DOCUMENTS

| | | |
|---|---|---|
| WO | WO 2011/017660 A2 * | 2/2011 |
| WO | WO 2012/153124 | 11/2012 |
| WO | WO 2013/119793 | 8/2013 |

OTHER PUBLICATIONS

Das et al., Zirconia Grafted Carbon Nanotubes Based Biosensor for M, Tuberculosis Detection, Applied Physics Letters, vol. 99, Issue 14, Sep. 5, 2011, 143702-1-143702-3.

Shahrokhian et al., Multi-Walled Carbon Nanotubes with Immobilised Cobalt Nanoparticle for Modifiction of Glassy Carbon Electrode: Application to Sensitive Voltammetric Determination of Thioridazine, Biosensors and Bioelectronics, vol. 24, Issue 11, Jul. 15, 2009, 3235-3241; Elsevier.

Phillips et al., point-of-Care Breath Test for Biomarkers of Active Pulmonary Tuberculosis, Tuberculosis, vol. 92, Issue 4, Apr. 9, 2012, 314-320.

Wen et al., Formaldehyde Gas Sensing Property and Mechanism of TiO2—Ag Nanocomposite, Physica B, vol. 405,Issue 19, Jul. 8, 2010, 4235-4239; Elsevier.

Perillo et al., The Gas Sensing Properties at Room Temperature of TiO2 Nanotubes by Anodization, Sensors and Actuators B: Chemical, vol. 171-172, May 12, 2012, 639-643.

Kao et al., A Sub-PPM Acetone Gas Sensor for Diabetes Detection Using 10 nm Thick Ultrathing InN FETs, Sensors 2012, vol. 12, May 29, 2012, 7157-7168.

Shin et al.. Exhaled VOCs Sensing Properties of WO3 Nanofibers Functionalized by Pt and IrO2 Nanoparticles for Diagnosis of Diabetes and Halitosis, J Electroceram, vol. 29, Aug. 16, 2012. 106-116.

Banerjee et al., The Detection of Imporovised Nonmilitary Peroxide based Explosives Using a Titania Nanotube Array Sensor, Nanotechnology vol. 20, Jan. 26, 2009, 1-6.

Seo et al., Gas Sensor Using Noble Metal-Loaded TiO2 nanotubes for detection of Large-sized Volatile Organic Compounds, Journal of Cermaic Society of Japan, vol. 119, Issue 11, Sep. 15, 2011, 884-889.

Seo et al., Microstructure Control of TiO2 Nanotubular Films for Improved VOC Sensing, Sensors and Actuators B: Chemical, vol. 154, Issue 2, Feb. 6, 2010, 251-256.

Zilberman et al., Carbon Nanotube/Hexa-peri-hexabenzocoronene Bilayers for Discrimination Between Nonpopular Volatile Organic Compounds of Cancer and Humid Atmospheres, Advanced Materials, vol. 22, Issue 38, Jun. 1, 2010, 4317-4320.

Metal Oxide Nanotubes (TiO2, ZnO2, SnO2): Bio and Chemical Sensors, www.utdalla.edu/~jxk041000/research/mox_nanotubes.html, accessed Oct. 9, 2013, 1 page.

PCT Application No. PCT/US13/67319, Filing Date Oct. 29, 2013, Swomitra M. Mohanty, International Search Report, dated Jan. 24, 2014, 15.

European Application No. 13851749.5, Filing Date Oct. 29, 2013, Swomitra M. Mohanty, European Search Report, dated Jun. 23, 2016, 10 pages.

* cited by examiner

FUNCTIONALIZED NANOTUBE SENSORS AND RELATED METHODS

RELATED APPLICATIONS

This application claims priority to U.S. Provisional Patent Application No. 61/795,850, filed Oct. 29, 2012, and U.S. Provisional Patent Application No. 61/861,107, filed Aug. 1, 2013 which are each incorporated herein by reference.

BACKGROUND

Noninvasive techniques for detection of pathogenic conditions of the human body are an area of growing interest in regards to rapid biosensing and diagnosis of diseases at the point of care (POC). These techniques are preferred for POC diagnosis as handling of traditional samples such as blood requires special skills and exposes the health care worker to possible blood borne pathogens. Ideally, non-invasive methods of diagnostics reduce this risk. To accomplish this, researchers have focused on screening external biological samples (i.e. saliva, urine, hair, sweat, and sputum) for biomarkers that indicate conditions such has diabetes, dehydration, and other diseases. Typical examples of biomarkers are antigens, antibodies, or proteins which require a liquid environment for analysis. As a result, diagnosis of diseases most often requires a liquid biological sample such as those mentioned above. However one class of biomarkers that is known to have associations with certain diseases, and yet has found limited use as a diagnostic tool is volatile organic biomarkers (VOBs). VOBs have been associated with different chronic and infectious diseases including tuberculosis (TB).

As a specific example, conventional methods for tuberculosis (TB) detection are traditionally performed in laboratories or hospitals. For example, the most common method for diagnosis of TB is the acid fast staining of clinical material, which is then followed by a sputum smear microscopy test. However, a disadvantage with the sputum smear test is its poor sensitivity, which is estimated to be at 70%. Additionally, the sensitivity of sputum smear spectroscopy in field settings has been shown to be much lower (e.g. 35%), especially in populations that have high rates of TB and HIV co-infection. Furthermore, drug susceptibility analysis of the mycobacterium cannot be determined from microscopy testing. This assessment is useful in determining the appropriate course of treatment for the patient. For this type of analysis culturing techniques are typically used.

Culturing of mycobacterium from sputum samples is a more sensitive technique. Sputum samples are collected and cultured in either solid media or liquid media looking for the presence of the mycobacterium. Drug resistant strains can be determined using this technique. However this methodology takes time to conduct (3-4 weeks for solid cultures, and 10-14 days for liquid cultures), which makes it difficult to employ in low resource settings that are typically far from testing facilities. Recently, other technologies have been developed including fluorescence microscopy for smear tests (10% more sensitive than light microscopy), LED fluorescent microscopy for inexpensive imaging equipment that can be used in the field without the need for a darkroom, and rapid culturing techniques to reduce incubation time. Despite the improvements that have been made in TB diagnosis, no simple inexpensive POC test is currently available. Accordingly, research continues for a fast, accurate, and inexpensive means for testing for TB.

SUMMARY OF THE INVENTION

The present invention provides for functionalized nanotube arrays, sensors, and related methods of detecting volatile organic compounds, volatile organic biomarkers, and other target compounds in an air environment, and biomarkers in a liquid environment. In one embodiment, a functionalized nanotube array is provided. The functionalized nanotube array can include a plurality of metal oxide nanotubes. The metal oxide nanotubes can be formed of a metal oxide and can have an interior or exterior surface that is functionalized with at least one metal ion.

In another embodiment, a sensor for detecting target compounds such as volatile organic compounds is provided. The sensor can include a nanotube array including a plurality of functionalized metal oxide nanotubes. The metal oxide nanotubes can be formed of a metal oxide and can have an interior or exterior surface that is functionalized with at least one metal ion and which is capable of binding with the target compounds. The sensor further includes a power source configured to apply a voltage to the nanotube array and a current sensor (e.g. potentiostat) configured to monitor and detect changes in a response current which varies upon binding with the target compounds.

In another embodiment, a method of detecting target compounds is provided. The method includes the steps of applying a voltage across a functionalized nanotube array, such as those described above, measuring a current passing over the functionalized nanotube array, flowing a gas over a functionalized nanotube array such that a target compound can bind with the at least one metal ion of the metal oxide nanotubes, monitoring the current for changes, and identifying a target compound found in the gas based on the changes in current.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the following drawings:

FIG. 3A shows a plot of the response of a cobalt functionalized TiO$_2$ sensor when exposed to humid air (made by bubbling N$_2$ gas through water and delivering it to the sensor) in relation to methyl nicotinate (10 mM dissolved in DI water, N$_2$ gas was used to carry the biomarker to the sensor by bubbling it through the solution.) Results show an order magnitude change from base line and that initial results indicate the sensor response to humidity is minimal when compared to methyl nicotinate.

FIG. 3B is a plot of the response of the Co functionalized TiO$_2$ sensor when exposed to N$_2$ followed by humid air, followed by methyl p-anisate (2.5 mM dissolved in DI water, delivered via N$_2$ carrier gas) in a single run. Once again an order of magnitude change in current is observed.

FIG. 3C is a plot of a second trial using the same conditions as shown in FIG. 3B, where the sensor was exposed to N$_2$ followed by humid air, followed by methyl p-anisate (2.5 mM dissolved in DI water, delivered via N$_2$ carrier gas).

DETAILED DESCRIPTION OF EXAMPLE EMBODIMENT(S)

Figure 1A:
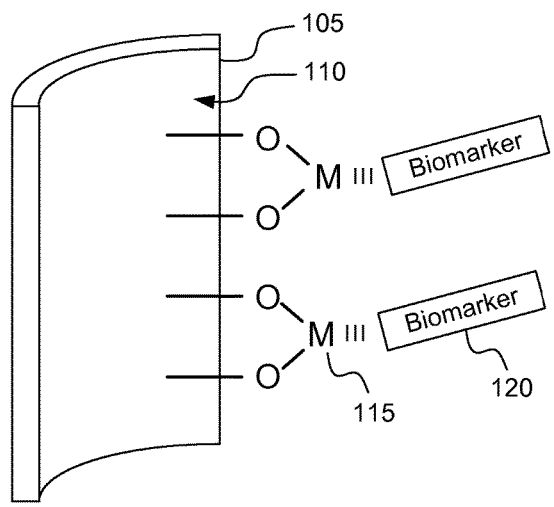
FIG. 1A is a schematic cutaway view of a section of functionalized nanotubes having metal ions and biomarkers associated therewith.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, the singular forms "a," "an," and "the" include plural referents unless the context clearly dictates otherwise. Thus, for example, reference to "a metal ion" includes one or more metal ion, reference to "an array" includes reference to one or more of such arrays, and reference to "a measuring step" includes reference to one or more of such steps.

Definitions

In describing and claiming the present invention, the following terminology will be used in accordance with the definitions set forth below.

In this disclosure, "comprises," "comprising," "containing" and "having" and the like can have the meaning ascribed to them in U.S. Patent law and can mean "includes," "including," and the like, and are generally interpreted to be open ended terms. The term "consisting of" is a closed term, and includes only the devices, methods, compositions, components, structures, steps, or the like specifically listed, and that which is in accordance with U.S. Patent law. "Consisting essentially of" or "consists essentially" or the like, when applied to devices, methods, compositions, components, structures, steps, or the like encompassed by the present disclosure, refers to elements like those disclosed herein, but which may contain additional structural groups, composition components, method steps, etc. Such additional devices, methods, compositions, components, structures, steps, or the like, etc., however, do not materially affect the basic and novel characteristic(s) of the devices, compositions, methods, etc., compared to those of the corresponding devices, compositions, methods, etc., disclosed herein. In further detail, "consisting essentially of" or "consists essentially" or the like, when applied to devices, methods, compositions, components, structures, steps, or the like encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments. When using an open ended term, like "comprising" or "including," it is understood that direct support should be afforded also to "consisting essentially of" language as well as "consisting of" language as if stated explicitly.

The term "about" as used herein, when referring to a numerical value or range, allows for a degree of variability in the value or range, for example, within 10%, or, in one aspect within 5%, of a stated value or of a stated limit of a range.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Where features or aspects of the disclosure are described in terms of a list or a Markush group, those skilled in the art will recognize that the disclosure is also thereby described in terms of any individual member or subgroup of members of the Markush group. For example, if X is described as selected from the group consisting of bromine, chlorine, and iodine, claims for X being bromine and claims for X being bromine and chlorine are fully described as if listed individually. For example, where features or aspects of the disclosure are described in terms of such lists, those skilled in the art will recognize that the disclosure is also thereby described in terms of any combination of individual members or subgroups of members of list or Markush group. Thus, if X is described as selected from the group consisting of bromine, chlorine, and iodine, and Y is described as selected from the group consisting of methyl, ethyl, and propyl, claims for X being bromine and Y being methyl are fully described and supported.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range includes "about 'x' to about 'y'". To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

As used herein, all percent compositions are given as weight-percentages, unless otherwise stated. When solutions of components are referred to, percentages refer to weight-percentages of the composition including solvent (e.g., water) unless otherwise indicated. As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

It is noted in the present disclosure that when describing the sensors, systems, or methods, individual or separate descriptions are considered applicable to one another, whether or not explicitly discussed in the context of a particular example or embodiment. For example, in discussing a particular sensor or system per se, the method embodiments are also inherently included in such discussions, and vice versa.

Functionalized Nanotube Sensors

In order to develop a successful volatile biomarker sensor for fast and accurate detection of volatile organic compounds, such as those associated with TB, several challenges have been overcome related to technological hurdles and implementation. Specifically, identifying appropriate elements for binding certain volatile biomarkers can be a challenge. Detection of volatile biomarkers is based on identifying appropriate binding elements with a high affinity for the biomarker. This also involves a fundamental understanding of the reaction between the biomarkers and the binding agent. Using electrochemical techniques such as cyclic voltammetry, cobalt has been identified for binding methyl nicotinate and methyl p-anisate. Sensitivity and selectivity can also be a challenge. For example, the human breath contains a variety of volatile organic compounds (VOC) at varying concentrations (i.e. acetone, methanol, ethanol, phenol, and others). The sensors described herein can function in the presence of these other compounds which are likely to be present during use of the sensor. Furthermore, the concentrations of VOCs in breath samples are typically on the order of parts per billion (ppb), therefore the sensor can also have a low limit of detection in the range of ppb. In a liquid environment target biomarkers can also be in such a range or higher and can demonstrate the same low limits of detection. The sensor is also reliable during operation under a wide variety of environmental conditions.

The described sensors provide for functionalized nanotube arrays, sensors, and related methods of detecting volatile organic compounds and biomarkers found in a fluid environment, including gaseous, vapor, and liquid environment detection. In one embodiment, a functionalized nanotube array is provided. The functionalized nanotube array can include a plurality of metal oxide nanotubes.

Referring to FIG. 1A, a section of a metal oxide nanotube 105 is shown. The metal oxide nanotubes can be formed of a metal oxide and can have an interior surface 110 and/or exterior surface that is optionally functionalized with at least one metal ion 115. The metal ions are chosen for selective binding with specific volatile biomarkers 120. In some embodiments, a native non-functionalized surface of the metal oxide nanotubes can bind with certain target compounds. In general, the sensors and methods using the metal oxide nanotubes can operate by detecting a change in electric current across the nanotubes. When the metal ions on the surface of the nanotubes bind with a target compound, such as a volatile biomarker, the electrical resistance of the nanotube array can change. When a bias voltage is applied to the nanotube array, the change in resistance can be detected as a change in current.

Figure 1B:
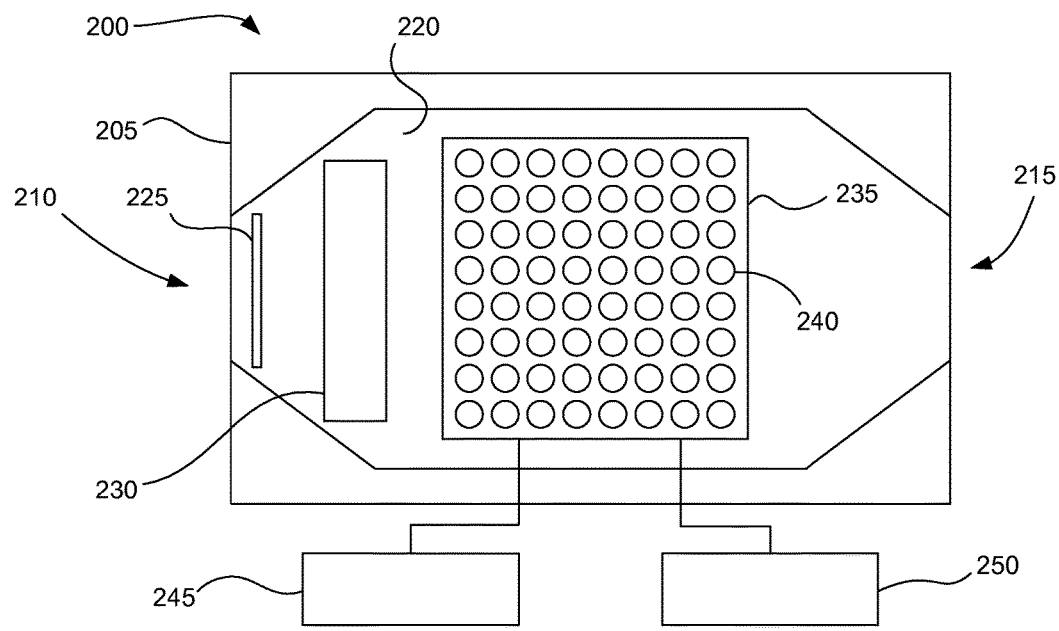
FIG. 1B shows a schematic of a generalized concept for a rapid electronic TB detection device having functionalized $TiO_2$ nanotube arrays that bind airborne volatile biomarkers for rapid TB diagnosis. A patient blows into the device and the biomarkers in the breath react with functionalized nanotubes that are under a bias voltage. The binding event between the biomarker and the functionalized nanotube causes a change in current which indicates a positive result.

A schematic drawing of a sensor which applies these principles is shown in FIG. 1B. The sensor 200 includes a housing 205 which can provide a platform and physical protection to components. The housing includes openings for an intake 210 and outlet 215. The intake directs sample fluid into an interior space 220 of the sensor, while the outlet allows sampled and excess fluid to exit the housing. Various additional components can be oriented within the interior space 220 of the housing. For example, a filter 225 can be oriented to remove particulates from sample fluid after entry through the intake. An optional concentrator 230 can be used to concentrate gases and/or vapors and to increase sampling signals. Further, an array 235 of metal ion functionalized metal oxide nanotubes 240 can be oriented along a path of the sample fluid which enters the housing. Although specific dimensions can vary considerably, the length of the housing can often be about 8 cm to about 10 cm. The array 235 of nanotubes can be connected to a power source 245 and a current sensor 250. As explained above, the power source and current sensor can be integrated into the sensor, in which case the power source and current sensor are located within the housing. Alternatively, one or both of the power source and current sensor can be external and can connect to the sensor through any suitable connection including wired or wireless power and communication.

Figure 2A:
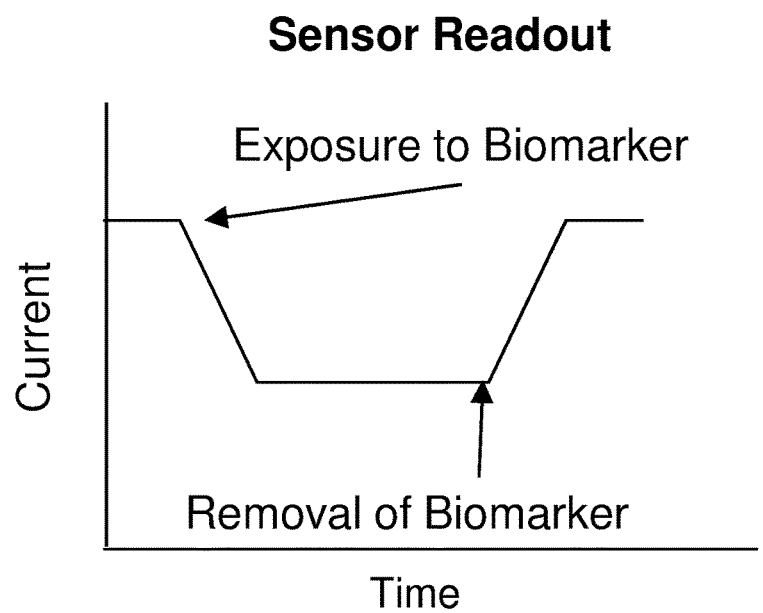
FIG. 2A shows a sensor readout indicating a positive test result based on a current drop during exposure to the biomarker.

A bias voltage is applied across the array of nanotubes 235 using the power source 245. For example, a set of electrode substrates can be oriented to contact the array of nanotubes at remote locations from one another. Such substrates can then be wired to a power source. The electrode substrates in some cases can partially obscure nanotube openings such that contact with target compounds primarily occurs on exterior surfaces of the nanotubes. However, contact along nanotube ends with electrode substrates can be irregular and allow for a portion of nanotube ends to be exposed while a remainder portion could be in full contact and obscured. When a target compound binds with the metal ions on the surface of the nanotubes 240, the resistance of the nanotubes changes. Typically, the resistance increases and the current decreases, although for some combinations of metal ions and target compounds resistance may decrease. For example, resistance may decrease with cobalt metal ions and alcohol based target compounds. FIG. 2A shows a conceptual sensor readout for a positive test result from the sensor when exposed to a target compound which is a biomarker. As the biomarker is introduced into the nanotube array, the current begins to drop and then remains at a lower current level until the biomarker is removed or the array is flushed with nitrogen, humid air or other suitable fluid which displaces the biomarker. Upon displacement, resistance of the array returns to initial levels.

The nanotubes disclosed herein can be made of a metal oxide or a combination of several metal oxides. In one aspect, the metal oxide can be a transition metal oxide. In another optional aspect, the metal oxide can be a metal or semi-metal selected from Group 13 or 14 and having an atomic number of 13 or greater (i.e. aluminum, silicon, gallium, germanium, indium, tin, thallium, and lead). Non-limiting examples of metal oxides that can be used to form the nanotubes include titanium dioxide, iron oxide, iridium oxide, tantalum oxide, zinc oxide, aluminum oxide, copper oxide, nickel oxide, chromium oxide, vanadium oxide, manganese oxide, zirconium oxide, palladium oxide, platinum oxide, cobalt oxide, lead oxide, silver oxide, tin oxide, magnesium oxide, and combinations thereof. In one embodiment, the metal oxide can be $TiO_2$. In another aspect, the metal oxide nanotubes can be formed of a single metal oxide.

Figure 2B:
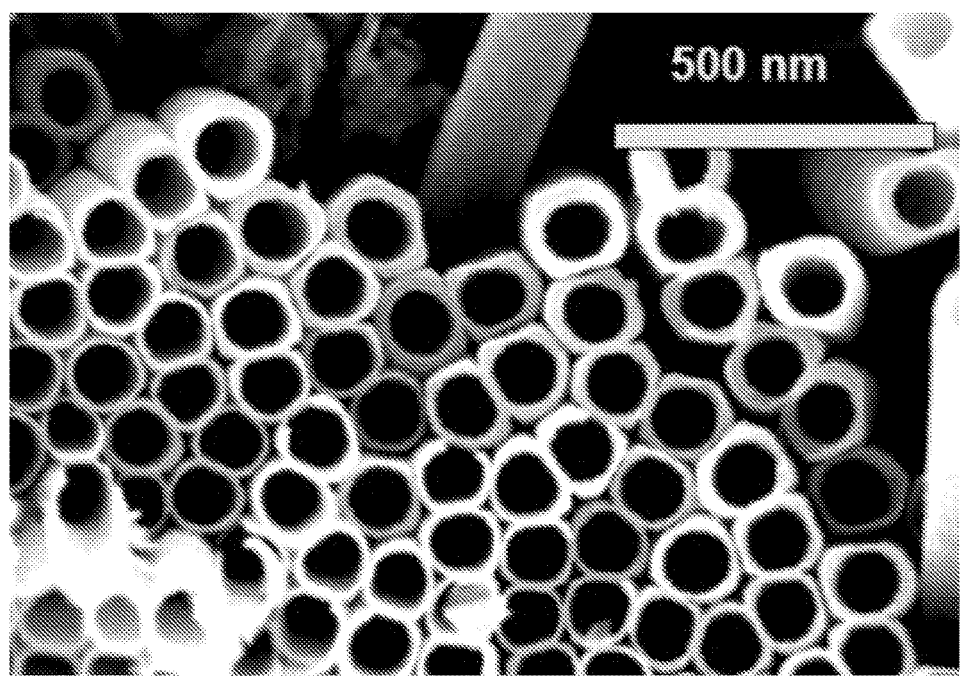
FIG. 2B is an SEM image of a self-ordered TiO$_2$ nanotube array (fabricated using anodization methods) for volatile biomarker sensing.

Typically, the metal oxide nanotubes are formed from anodized metal. For example, $TiO_2$ nanotubes can be prepared, in some embodiments, by ultrasound assisted anodization. In one embodiment, a titanium foil anode and a platinum cathode can be used to form titanium nanotubes. An image of $TiO_2$ nanotubes prepared using this method is shown in FIG. 2B. Varying the anodization potential can control the diameter of the tubes, and changing the anodization time can vary the length of the tubes. Although dimension can vary for different materials and process conditions, diameters of the nanotubes can often range from about 20 nm to about 500 nm; lengths can often range from about 0.5 µm to about 50 µm; and wall thicknesses can range from about 5 nm to about 200 nm. The nanotubes can form ordered arrays of commonly aligned and oriented nanotubes. In one aspect, the array of nanotubes can be arranged with adjacent nanotubes substantially parallel to one another and stacked contacting one another. Ultrasonication during the anodization process can also result in improved ordering of the stacked nanotubes.

Metal oxide nanotubes can be annealed in oxygen to increase the resistance of the nanotubes. For example, in one embodiment the as-anodized $TiO_2$ nanotubes can be annealed in oxygen at 500° C. for 6 h to increase electrical resistance, although other temperatures and times can be used depending on the materials. As a general rule, annealing temperatures from about 200° C. to 600° C. can be used with annealing times from about 1 to 10 hours. Increasing the resistance of the nanotubes can enhance current changes which will be detectable when the nanotubes are sufficiently biased and as binding events occur between the functionalized nanotube and a target compound such as a volatile biomarker.

The nanotubes can be functionalized with at least one metal ion that is capable of binding a target volatile organic compound. Non-limiting examples of metal ions that can be utilized to functionalize the disclosed nanotubes include $Cu^{1+}$, $Li^{1+}$, $Fe^{2+}$, $Ni^{2+}$, $Cu^{2+}$, $Co^{2+}$, $Pb^{2+}$, $Fe^{3+}$, $Co^{3+}$, $Cr^{3+}$, $Mn^{3+}$, $Ni^{3+}$, $Sc^{3+}$, $Sb^{3+}$, $Ni^{4+}$, $Mn^{4+}$, $Ti^{4+}$, $As^{4+}$, $Sb^{4+}$, $Pt^{4+}$, $Au^{1+}$, $Zn^{2+}$, $Pd^{2+}$, $Pd^{4+}$, $Ag^{1+}$, and combinations thereof. In one alternative, the metal ions can be monovalent: $Li^{1+}$, divalent: $Fe^{2+}$, $Ni^{2+}$, $Cu^{2+}$, $Co^{2+}$, $Pb^{2+}$, trivalent: $Fe^{3+}$, $Co^{3+}$, $Cr^{3+}$, $Mn^{3+}$, $Ni^{3+}$, $Sc^{3+}$, $Sb^{3+}$, or tetravalent: $Ni^{4+}$, $Mn^{4+}$, $Ti^{4+}$, $As^{4+}$, $Sb^{4+}$, $Pt^{4}$. In one embodiment, the metal ion can include $Co^{2+}$. In another aspect, the metal ion can include cobalt, chromium, copper, zinc, iron, nickel, palladium, gold, or combinations thereof. Although mixtures of ions can be used, in one aspect, the metal ions can be uniformly a single metal ion. Metal ions can be selected based on their ability to bind with a target compound. Computational modeling can be used to predict the affinities of various metal ions with various biomarkers. Metal ions can also be tested experimentally using cyclic voltammetry methods such as the method explained in the Examples below. Non-limiting examples of specific metal ion and target compound pairs include chromium and methyl nicotinate, copper and glutathione, cobalt and glutathione, nickel and lactic acid, cobalt and lactic acid, and the like.

The metal oxide nanotubes can be functionalized with the metal ion or ions by metal ion exchange methods known in the art. Exchanging metal ions (Co, Zn, Cr, etc.) onto the $TiO_2$ nanotube surface is made possible by the presence of large numbers of hydroxyl (Ti—OH) groups at the surface. These hydroxyl groups are exchangeable sites for binding metal ions. A surface hydroxyl proton is exchanged with a metal ion, binding the metal ion to the nanotube surface. Generally, the ion exchange can be performed by soaking the nanotubes in a solution containing the metal ion. In one embodiment, $TiO_2$ nanotubes can be functionalized with cobalt(II) ions by first heating the nanotubes to 100° C. to dehydrate the nanotubes, then soaking the nanotubes for 30 minutes in a solution of 0.5 wt % cobalt(II) chloride in ethanol, then rinsing the nanotubes and drying in a vacuum oven at 100° C. The time period for soaking the nanotubes in the metal ion solution can vary from about 30 minutes to about 5 hours.

Optionally, the metal oxide nanotubes can be non-functionalized such that a native surface of the nanotubes binds with a target compound. Thus, at least one of the interior and exterior surface binds with the target compound either via native surface or metal ions functionalized on these surfaces. For example, ammonia and nitrates can be readily detected using non-functionalized metal oxide nanotubes, especially titanium oxide nanotubes. Other target compounds can also be detected using metal oxide nanotubes in a similar manner.

In another embodiment, a sensor for detecting target compounds is provided. The sensor can include a nanotube array including a plurality of functionalized metal oxide nanotubes. The metal oxide nanotubes can be formed of a metal oxide and can have an interior or exterior surface that is optionally functionalized with the metal ion. The nanotube surface or metal ions are capable of binding with the target compounds. The sensor further includes a power source configured to apply a voltage to the nanotube array and a current sensor configured to monitor and detect changes in a response current which varies upon binding with the target compounds. The current sensor can be any instrumentation which is capable of measuring current such as a potentiostat or the like.

Target compounds can be determined in advance of the manufacturing of the nanotubes or sensor devices disclosed herein. Selection of the metal ions used in the functionalized nanotubes can be based on the target compound(s) selected for detection. The nanotubes and sensors disclosed herein can be utilized to detect a wide range of target compounds such as volatile organic compounds and/or non-volatile compounds. Accordingly, the sensor can be used to detect target compounds within a fluid, including both gaseous and liquid environments. Non-limiting examples of classes of compounds that can be detected can include compounds associated with explosives, such as those associated with IED-type devices such as peroxides, nitrates, and the like, compounds associated with drinking water contamination such as trichloroethylene or arsenic, and compounds that are biomarkers for a physiological condition or disease. Non-limiting examples of physiological conditions or diseases that can be diagnosed through the detection of associated volatile organic compounds in a subject's breath include tuberculosis, breast cancer, lung cancer, heart disease, diabetes, preeclampsia, oxidative stress, and combinations thereof. When the volatile organic compound is a biomarker for a physiological condition or disease the biomarker can be present in the breath of a subject. Thus, detection of the biomarker can be achieved by passing the expelled breath of the subject over the nanotubes in a sensor. Non-limiting examples of specific biomarkers can include methyl phenylacetate, methyl p-anistate, methyl nicotinate, o-phenylanisole, lactic acid, reduced or oxidized glutathione, uric acid, urease and combinations thereof. Methyl phenylacetate, methyl p-anistate, methyl nicotinate, o-phenylanisole, are known biomarkers for TB. Reduced and oxidized forms of glutathione are known biomarkers for oxidative stress in a subject. Other target compounds that can be tested include trichloroethane, arsenic, selenium, and the like.

The sensors disclosed herein can have a power source that is configured to apply a voltage (e.g. bias voltage) of about −5 V to about 10 V, in some cases up to 5 V, and in some cases −0.2 V to about −0.8 V. The applied voltage can be selected depending on the target volatile organic compound(s) targeted for detection by the sensor. The power source can be a direct current or alternating current power source. In one embodiment, the power source is a battery. In some embodiments, the sensor can be a self-contained device that includes a built-in rechargeable, disposable, or replaceable battery. In other embodiments, the power source can be external and connect to the sensor through wires. The current sensor can also be integrated or external. In one embodiment, the sensor for detecting target compounds can connect to an external power source and current sensor. The sensor can thus be manufactured more cheaply and can be disposed of after one or more uses, without disposing of the power source or current sensor. In some embodiments the power source and current sensor can be a single device that plugs into the sensor. Such a device can include integrated controls or the device can be configured to be controlled by a personal computer, laptop, smart phone, etc. Such a device can also display results from the sensor in several ways. For example, the device can display a graphical representation of the current signal from the sensor. Alternatively, the device can simply indicate a "yes" or "no" to whether the target compound is present through a LED, auditory buzzer, or the like.

In one embodiment, the sensors disclosed herein can include a sample intake configured to direct flow of a sample gas (or fluid) over the nanotube array of the sensor. The intake can be configured to sample ambient air or can be configured to receive a breath from a subject. In such embodiments, the air intake can include a particle filter to remove small particulate matter (PM10 and/or PM2.5) which can clog or otherwise limit the functionality and/or useful life of the sensor. The inlet can also include a concentrator configured to concentrate the air intake so as to increase the sensitivity of the sensor. A non-limiting example of concentrator includes using solid extraction fibers which bind to volatile organic compounds which are then subsequently released. A molecular filter, charged chromatography column, and the like can also be used.

The sensor can include a housing to contain the various components of the sensor. The filter, concentrator, and nanotube array can be oriented inside an interior space of the housing. The housing can contain the gas sample so that the sample can pass across and react with the functionalized nanotubes. The housing can also have an outlet for the gas sample to flow out from the housing. In one aspect, the intake and outlet can be disposed on opposite sides of the nanotube array so that the sample gas flows across the nanotube array. In embodiments where the sample is expired breath from a subject, the subject can breathe into the intake. The intake can include a mouthpiece configured in size and shape to comfortably fit into the mouth of the subject to allow the subject to breath into the sensor. In some embodiments the intake can also include a one-way valve to prevent backflow of gases out through the intake. The mouthpiece can optionally be disposable or replaceable and configured to engage with the intake. The outlet can also include a valve that allows air to pass through when the subject is blowing but then prevents air from escaping from the housing during the testing period. In this way the expired breath, and the target biomarkers therein, can be prevented from flowing or diffusing out of the housing during testing. In other embodiments, the sample gas can be recirculated across the nanotubes, such that the target compounds will have additional opportunity to bind with the metal ions.

The sensors disclosed herein can be reusable or can be manufactured to be disposable. When the sensor is configured to be reusable, the sensor can also include an ultraviolet light source which can be activated in order to shine ultraviolet light on the functionalized nanotubes following use of the sensor. The ultraviolet light can cause the target compounds bound to the metal ions to be released so that the sensor can be reused. Alternatively, the sensor can have a transparent housing and an external ultraviolet light source can be used. When configured to be disposable, the sensor can be made of inexpensive materials including some or all of the materials being biodegradable.

In another embodiment, a method of detecting target compounds is provided. The method includes the steps of applying a voltage across a functionalized nanotube array, such as described above, measuring a current passing over the functionalized nanotube array, flowing a gas over the functionalized nanotube array such that a target compound can bind with the at least one metal ion of the metal oxide nanotubes, monitoring the current for changes, and identifying a target compound found in the gas based on the changes in current. The sensors and nanotubes described above can be utilized in the method of detecting described herein. In one embodiment, the method of detecting can further include the step of diagnosing the human subject with a physiological condition or disease based on the identifying of the biomarker. In another embodiment, the method of detecting can further include utilizing a sensor that is reusable. Therefore, in these embodiments the method can further include exposing the functionalized nanotubes to ultraviolet light. The exposure of the functionalized nanotubes to the ultraviolet light can cause any target compounds bound to the metal ions to be released.

EXAMPLES

Example 1—Sensor System

Methods for detecting the volatile biomarkers for tuberculosis already exist (gas chromatography, mass spectrometry), but these are not appropriate for low resource settings at the POC. There is a clear technological gap that can be filled by use of the disclosed sensors and methods. In this example, the sensor is a portable breathalyzer device (e.g. one that is approximately 8 to 10 cm in length and width or smaller) that contains arrays of $TiO_2$ that are functionalized with different elements for detecting different types of volatile biomarkers given off by mycobacterium that reside in the lungs. The electronic response of the device is on the order minutes per test. This rapid response time is orders of magnitude faster than any test currently in use. Furthermore the nanotube sensing element described here can be regenerated and reused which further reduces the cost per test and reduces the cost of waste disposal which adds to the overall cost of the device.

In this specific embodiment, the $TiO_2$ nanotubes can be functionalized with cobalt(II) ions. This type of sensor for tuberculosis biomarkers has advantages as compared to prior technologies. For example, TB can be detected based on the presence of VOBs (volatile biomarkers) immediately; fast detection time of less than several minutes; portable and simple to operate; and can be deployed in resource limited settings and used to quickly screen large numbers of subjects within a community.

In addition the disclosed sensors and systems can be adapted for detection of other medical conditions that exhibit volatile organic biomarkers such as heart transplant rejection, lung cancer, ischemic heart disease, preeclampsia of pregnancy, diabetes mellitus, and breast cancer. Volatile biomarkers associated with such conditions can include, but are not limited to, acetone, alkanes, alkane derivatives, alkenes, ammonia, mercaptans, fatty acids, and the like.

Example 2—Preliminary Studies

Preliminary studies using cyclic voltammetry methods identified cobalt (II) as being a leading candidate for binding methyl nicotinate and methyl p-anisate. These methods showed suitable bias voltages of −0.2 V and −0.8 V for methyl nicotinate and methyl p-anisate respectively. These voltages gave the maximum signal during detection and can be used to change the selectivity of the sensor in the presence of multiple volatile organic markers. $TiO_2$ nanotubes were then synthesized using electrochemical anodization and functionalized with cobalt (II) using metal ion exchange methods previously described.

Figure 3A:
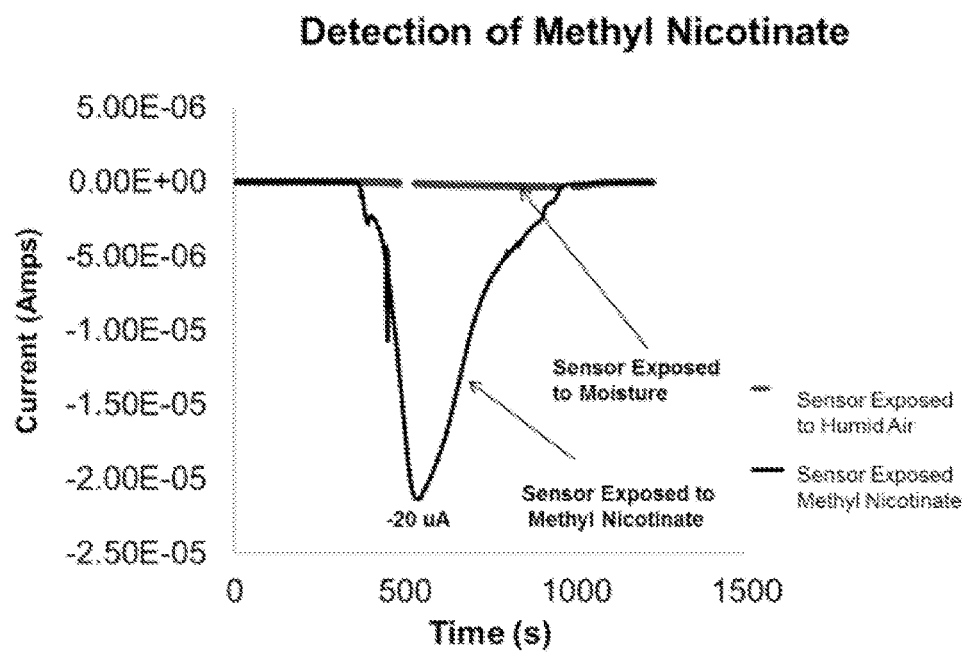
FIGS. 3A-3C show preliminary results for detection of TB volatile biomarkers methyl nicotinate and methyl p-anisate.
Figure 3B:
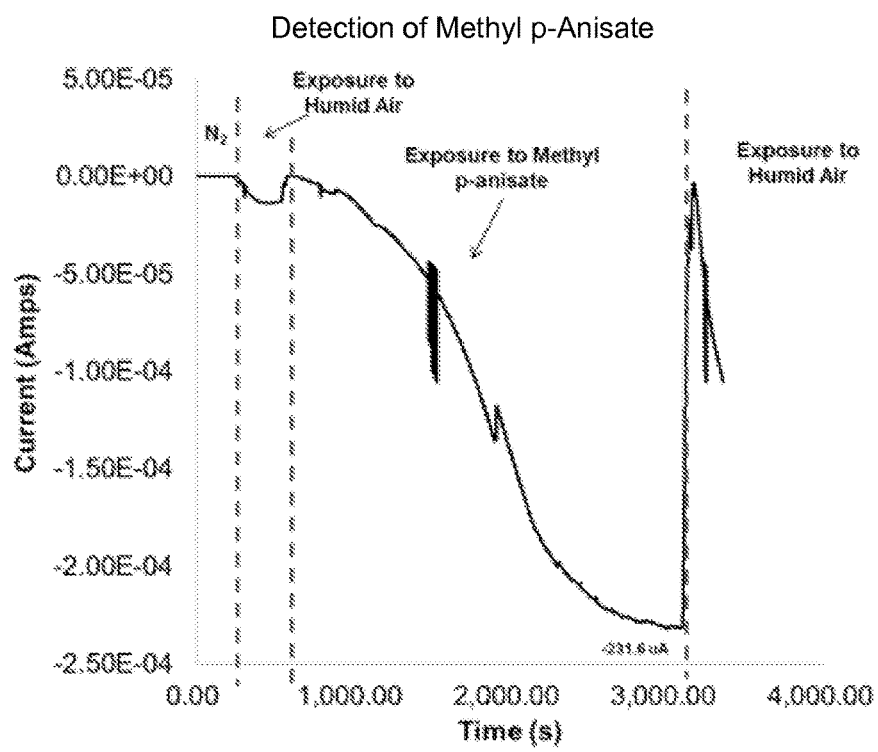
Figure 3C:
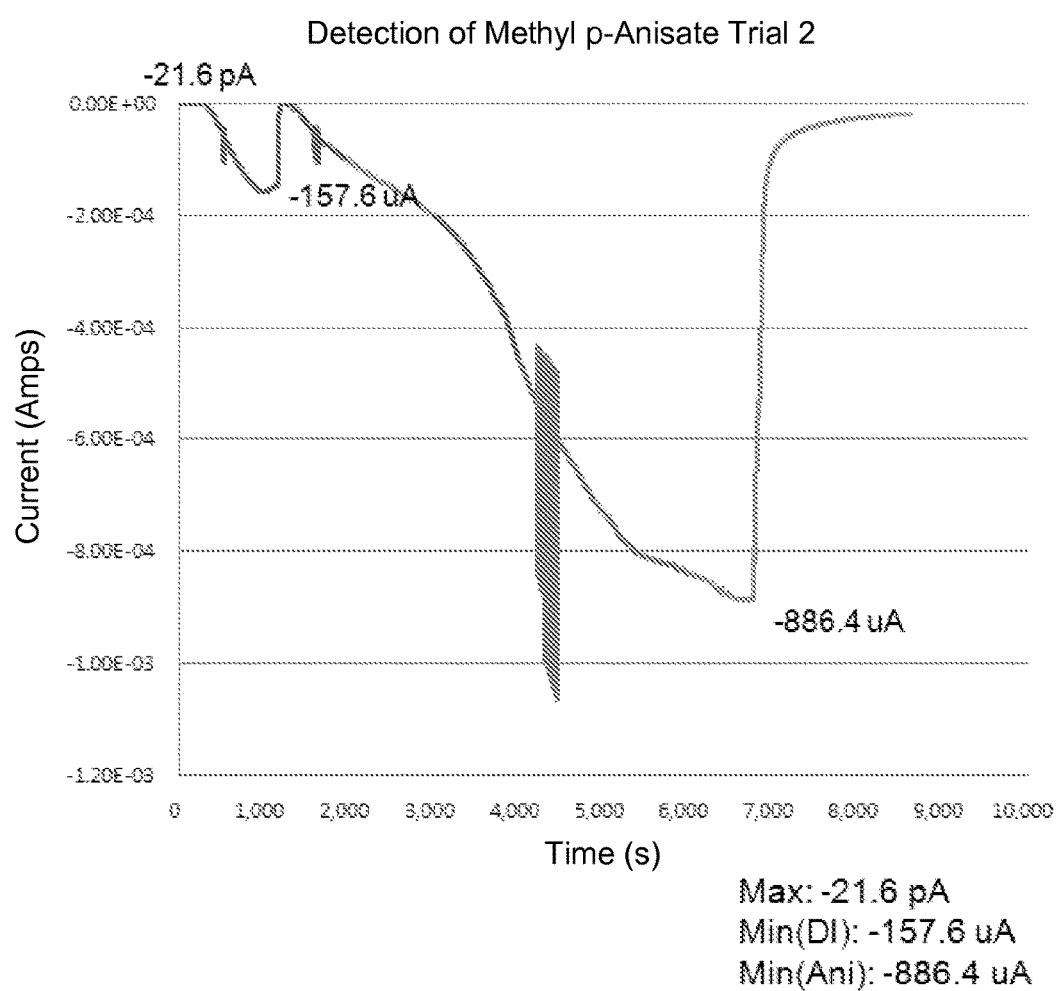

Briefly, cobalt(II) chloride is dissolved in ethanol and a $TiO_2$ nanotube array is incubated in the solution for several hours before drying in a vacuum oven. This results in cobalt (II) on the surface of the nanotubes. The cobalt (II) is a strong oxidizer and reacts with the methyl nicotinate and methyl p-anisate. FIGS. 3A and 3B show preliminary results for cobalt (II) functionalized $TiO_2$ nanotubes. In these preliminary experiments, the biomarkers were dissolved in water and then delivered to the sensors by bubbling $N_2$ gas through the solution. The sensors were exposed to humid air by bubbling $N_2$ gas in the same way but through pure water. FIG. 3A shows the current vs. time when two identical sensors were exposed to humid air and methyl nicotinate. As seen in the figure, the sensor exposed to methyl nicotinate exhibited a change in current of about −20 µA, while the sensor exposed to humid air remained nearly constant. FIG. 3B shows results from a single sensor exposed to humid air followed by methyl p-anisate in sequence. FIG. 3B shows a slower response time for detecting methyl p-anisate than for methyl nicotinate. This could be due to the different testing conditions between the experiments. However, FIG. 3B shows that the response to methyl p-anisate is much greater than the response for humid air. FIG. 3C shows a second trial run at the same conditions as the trial shown in FIG. 3B. The magnitude of the change can be correlated to differences in concentration. Results show that the cobalt (II) functionalized $TiO_2$ nanotubes are capable of detecting the biomarkers when derived from chemical mimics dissolved in water and delivered to the sensor by bubbling $N_2$ gas through the solution as it reaches the sensor. Results also show that the sensor response to humidity is minimal when compared to the biomarker under same testing conditions.

Example 3—Specificity

Figure 4A:
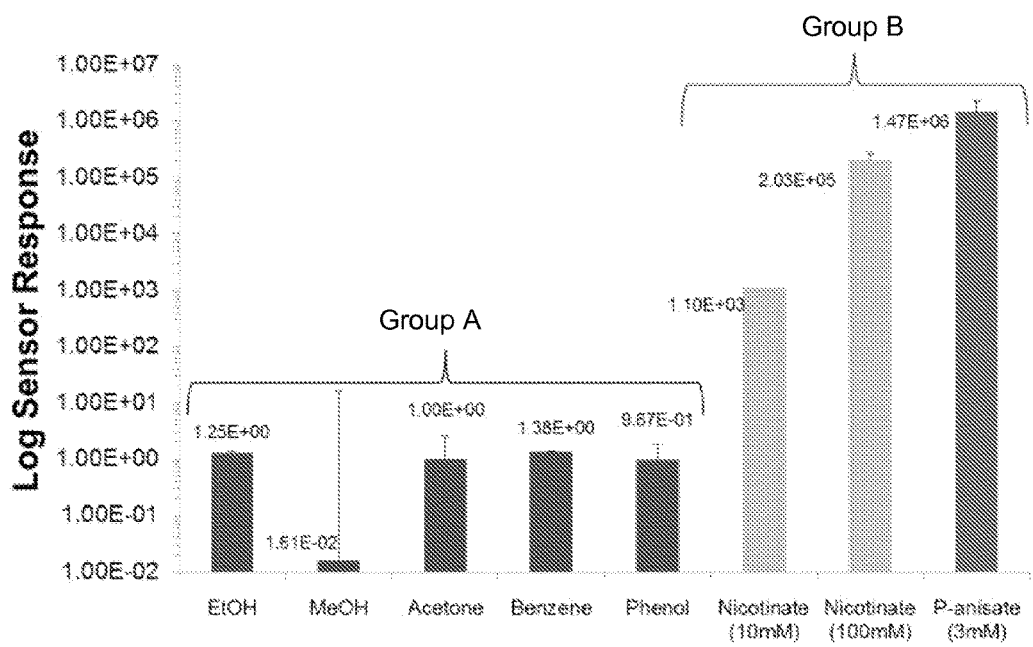
FIG. 4A shows a plot of responses of an embodiment of a cobalt functionalized TiO$_2$ nanotube sensor when exposed to concentrated levels (20 ppm) of common VOCs found in breath and volatile biomarkers associated with TB. Sensors show little response when exposed to common VOCs. However when exposed to methyl nicotinate and p-anisate, a response ranging from 3-6 orders of magnitude difference is shown. These results show the sensor is specific for the target volatile biomarkers.

As mentioned previously the human breath is a complex mixture of gases with several VOCs present. Preliminary tests were carried out to determine the specificity of the sensor when exposed to VOCs found in the breath including ethanol, methanol, acetone, benzene, and phenol. Typically these compounds are found at the ppb range in the breath of humans. However for preliminary testing concentrated sources (20 ppm) of the each of these compounds was used and delivered to the $TiO_2$ sensor in four separate experiments (the sensor was only exposed to one VOC at a time and not in a complex mixture). FIG. 4A shows the sensor response for each of the compounds tested.

Response is defined as: $(I_d-I_b)/I_b$, where $I_d$ is the current measured when the sensor is exposed to a volatile compound and $I_b$ is the baseline current before detection. Results are shown for concentrated VOCs commonly found in the breath (designated as "Group A") and for VOBs associated with TB (designated as "Group B"). The sensor response to ethanol, methanol, acetone, benzene, and phenol ranged from 0.6 to 1.38 indicating these compounds have little effect on the sensor when operated at conditions specific for TB volatile biomarkers (20° C. and 130 SCCM flow rate). However, when the sensor was exposed to methyl nicotinate (10 mM and 100 mM) a $10^3$ and $10^5$ change is observed in response respectively. In addition P-anisate showed a $10^6$ change in response. This indicates that the sensor is specific for the TB biomarkers and has the potential to detect these molecules in the presence of other VOCs that are found commonly in human breath.

Figure 4B:
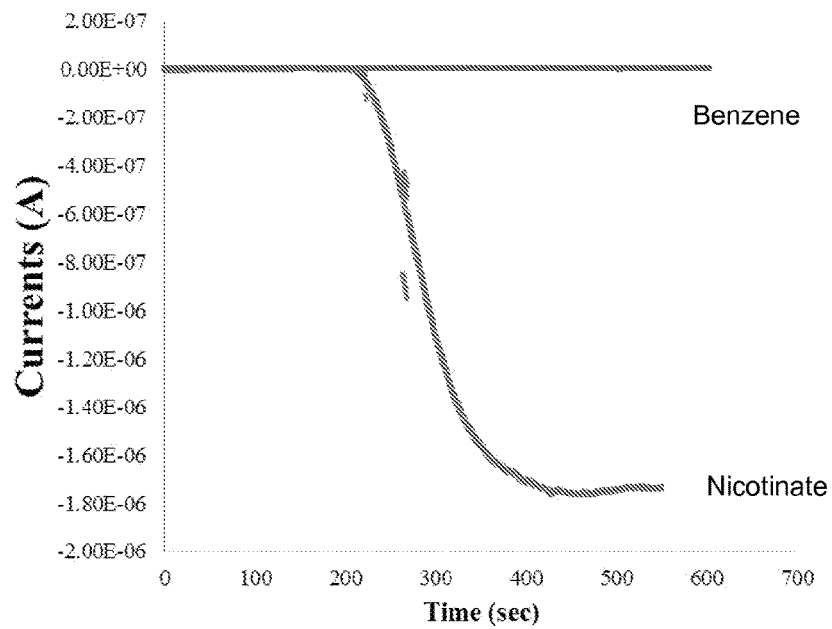
FIG. 4B shows plots of current vs. time for a common TiO$_2$ sensor exposed to benzene and methyl nicotinate. Nicotinate was exposed at 5 ppm, while benzene was exposed at 20 ppm.

FIG. 4B shows plots of current vs. time for a $TiO_2$ sensor exposed to benzene and methyl nicotinate and 20 ppm. As can be seen from this plot, the sensor is able to clearly distinguish between nicotinate and benzene and exhibits substantially no response to benzene exposure.

Example 4—Identification and Characterization of Elements that Interact with the Candidate Volatile Biomarkers Using Computational Calculation Using computational modeling techniques, this experiment studies metal interaction with VOBs to identify the metals with high affinity towards the biomarkers. Preliminary results indicate cobalt (II) is a suitable metal candidate for methyl nicotinate and methyl p-anisate. Studies can be used to screen and select specific metal ions for use with specific biomarkers. Lastly the selectivity issue for the sensor can be addressed by determining the relative binding strength for volatile organic compounds (VOCs) such as isopropanol, acetone, and methanol which are commonly found in human breath.

The sensor device is based on metal ion functionalized titanium dioxide nanotubes, where the nature of the metal ion determines whether or not VOB detection takes place. The metal-biomarker interaction prompts a change in the electrical resistivity of the sensing material, allowing the sensor to detect the biomarker based on changes in electric current through the sensing material. The evaluation and identification can be done for a set of metal ions {monovalent: $Li^{1+}$, divalent: $Fe^{2+}$, $Ni^{2+}$, $Cu^{2+}$, $Co^{2+}$, $Pb^{2+}$, trivalent: $Fe^{3+}$, $Co^{3+}$, $Cr^{3+}$, $Mn^{3+}$, $Ni^{3+}$, $Sc^{3+}$, $Sb^{3+}$, tetravalent: $Ni^{4+}$, $Mn^{4+}$, $Ti^{4+}$, $As^{4+}$, $Sb^{4+}$, $Pt^{4+}$) selected on the basis of Hard-Soft-Acid-Base principle. Based on this principle, a hard acid (small atomic/ionic radius, high oxidation state, low polarizability) binds a hard base more strongly. Since oxygen is considered a hard base, one can choose a hard acid for effective bonding.

The study can be done in gas phase (in the absence of solvent) and as well as liquid phase (in the presence of a solvent molecules as the VOBs of interest come from the lungs which is moist air). The structural and energy aspects determined in gas phase make the basis for calculation in liquid phase. In gas phase, the metal-biomarker interaction can occur via the lone pair electrons of the oxygen. However, in liquid solvent, the binding might occur via the anionic oxygen of the biomarker, presuming the dissociation of the biomarker in solution.

For modeling of solvent effects, adaptations of three modeling schemes can be used: 1) Polarizable continuum model (PCM) where the long-range electrostatic solvation effects are considered. 2) Incorporation of explicit water molecules surrounding the metal-biomarker system (most similar to the expected operating conditions of the sensor) explains the short range solvent effects well. However, the inclusion of a large number of solvent molecules can be complex and computationally demanding. 3) A modeling scheme including the above two methods which can take care of both short and long range solvent effect. This scheme can be modeled with a smaller number of explicit solvent molecules compare to the second scheme, but long range solvent effects can be taken care of by PCM.

The free energy of binding in gas phase is calculated using the electronic energy, zero point energy (ZPE) and entropy terms corresponding to translational, vibrational and rotational motion of the system. The gas phase and liquid phase binding free energy, $\Delta G^*_B(gas)$ and $\Delta G^*_B(liquid)$, are calculated using Eqn. 1 and Eqn. 2 respectively from FIG. 5 where:

X=methyl nicotinate, methyl p-anisate, methyl phenyl acetate, o-phenyl anisole

M=$Cu^{1+}$, $Fe^{2+}$, $Ni^{2+}$, $Cu^{2+}$, $Co^{2+}$, $Pt^{2+}$, $Fe^{3+}$, $Co^{3+}$, $Cr^{3+}$, $Mn^{3+}$, $Ni^{3+}$, $Sc^{3+}$, $Sb^{3+}$, $Ni^{4+}$, $Mn^{4+}$, $Ti^{4+}$, $As^{4+}$, $Sb^{4+}$, $Pt^{4+}$ $\Delta G^*_B(gas)$=Free energy of binding in gas phase (without solvent), * denotes the standard state $\Delta G^*_B(liquid)$=Free energy of binding in liquid phase (with solvent)

Figure 5:
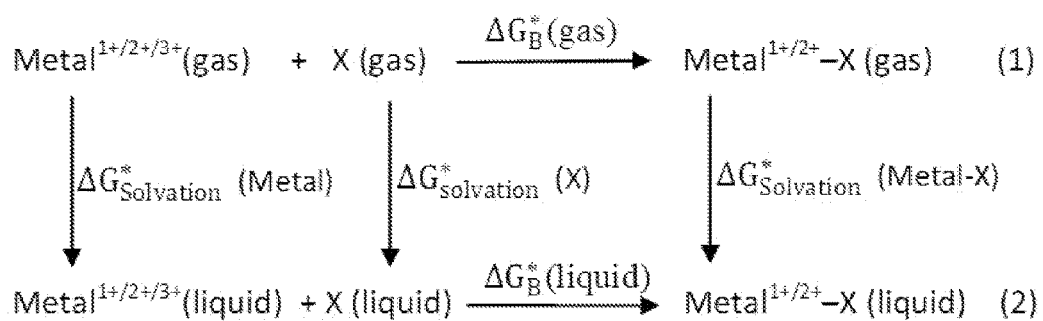
FIG. 5 shows a schematic presentation of reactions and terms involved in metal-biomarker binding.
Figure 6:
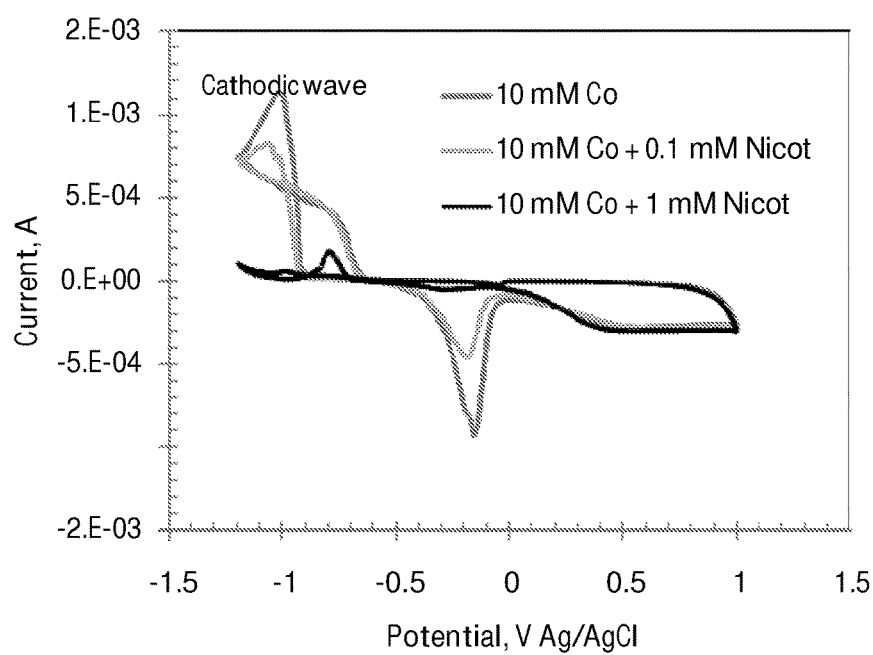
FIG. 6 shows preliminary results of a cyclic voltammetry (CV) method for screening of Co(II) solution with and without additions of methyl nicotinate: A CV of Co(II) with 0 mM, 0.1 mM, and 1 mM additions of methyl nicotinate. Results indicate Co binds nicotinate at a voltage of −0.2 V. This method can be used to screen other potential binding elements for the methyl phenylacetate, and o-phenylanisole and identify the operating voltage for detection of the specific biomarker.

$\Delta G^*_{solvation}(Metal)$=Solvation free energy for metal ion, $\Delta G^*_{solvation}(X)$=Solvation free energy for biomarker $\Delta G^*_{solvation}(Metal-X)$=Solvation free energy for metal-biomarker The solvation free energy is basically the energy released when one mole of solute (in this case metal, biomarker and metal-biomarker complex) is solvated in aqueous solution. Solvation involves various types of intermolecular interactions: hydrogen bonding, ion-dipole, and dipole-dipole attractions or van der Waals forces. Solvation free energy for the species involved in Eqn. 1 of FIG. 5 is useful in determining binding free energy in liquid phase as shown below (Eqn. 3):

$$\Delta G^*_B(liquid)=\Delta G^*_B(gas)+[\Delta G^*_{solvation}(Metal\text{-}X)- (\Delta G^*_{solvation}(Metal)+\Delta G^*_{solvation}(X))] \quad (3)$$

This procedure can be adapted for all the metal ions listed above and a detailed comparison of relative strength of interaction for different metal-biomarker complexes can be made. The understanding of the binding phenomena can be characterized quantitatively through structural analysis and charge distribution in the system and qualitatively via the orbital interactions occurring in the binding site. The free energy of binding obtained from the above methodology can be helpful in determining the oxidation potential generated due to change in oxidation state of the metal. The oxidation potential for the above reaction of Eqn. 2 of FIG. 5 can be calculated using Nernst Equation:

$$E_0(\text{volt}) = -\frac{\Delta G^*_B(\text{liquid})}{nF} \quad (4)$$

where $E_0$=Oxidation potential, n=number of electrons involved in reaction, F=Faraday constant The result thus obtained can be compared and validated with the cyclic voltammetry study conducted for the same process. The best three metals determined from this study can be further used in sensor devices.

The following computational modeling can be accomplished using Density Functional Theory (DFT) and Ab Initio (MP2) methodology as implemented in the Gaussian program package. To carry out the DFT computation, different exchange correlation functionals such as PBE, BP, and B3LYP can be implemented. In addition, suitable pseudo potentials can be used such as LanL2DZ for transition metals and 6-31G+** basis sets for small atoms. The ZPE can be calculated for Eqn. 1 and Eqn. 2 for determining the binding free energy. The solution modeling can be done with the PCM based solvation model UNIVERSAL as implemented in Gaussian09. Geometry optimizations can be iterated until forces are less than $10^{-5}$ au and energy convergence is $10^{-6}$ hartree. Vibrational frequencies can be calculated at the optimized geometry to validate the stable structure. The charge analysis can be performed with Muliken charges and Natural Bond Order analysis. Molecular orbital interactions can be analyzed qualitatively as well as quantitatively via the molecular orbital theory approach.

Example 5—Verification and Characterization of Modeled Metals that Interact with the TB Volatile Biomarkers Using Electrochemical Methods Metal ion functionalized metal oxide nanotubes can be stable, and have a long shelf-life (such as 6 months) so sensors shipped all over the world can be stored for extended periods of time. To accomplish this, inorganic elements identified from the modeling done in Example 4 can be investigated for nanotube functionalization as they are stable and known to bind organic molecules at different affinities. Of particular interest for detecting TB volatile biomarkers are Co, Cr, Ni, and Zn. Further, sensors can be vacuum sealed until used to reduce chances of inadvertent binding with stray compounds or decreases in sensitivity.

Electrochemical Studies

Cyclic voltammetry methods can be used to verify the binding ability of metals for methyl phenylacetate, and o-phenylanisole. The biomarkers of interest for detection of TB with high confidence are essentially organic esters. It is noted that esters can be detected electrochemically using cyclic voltammetry. Some esters can be electro-oxidized, depending on the type of ester and molecular structure. The biomarkers can be oxidized using an appropriate electrolyte system consisting of a supporting salt (e.g., perchlorate) with pH adjustment. During electro oxidation, each biomarker can yield distinct anodic waves with peaks occurring at different potentials. From the integrated anodic current vs. time, the charge released can be calculated. Concentrations of the biomarkers can be determined from the anodic charge calculations using Faraday's law with an assumption that all the charges are attributed to oxidation of the biomarkers. Conducting differential cyclic voltammetry can alleviate the error due to double layer charging during cyclic voltammetry. These electrochemical techniques can be used for detection of biomarkers in the laboratory. However, for a POC device, preparation of electrolyte containing the biomarkers from the breath sample can be difficult. Therefore, a technique involving direct analyses of breath samples in gaseous form can be more useful. In order to achieve this, complexation of biomarkers with metal cations is considered. It is reported that adsorption of organic molecules on the metal cations leads to oxidation of the organic species. For example, it has been observed that Fe(III), Cu(II) and $VO^{2+}$ cations cause oxidation of anisole adsorbed on the surface. It is also well known that ability of complex formation and stability of the complex with metal ions is associated with how strong an oxidizer the metal ion is. Therefore, metal cations can be effectively used for complex formation with the volatile biomarkers.

The ordered arrays of $TiO_2$ nanotubes are an excellent support for the metal ions for binding with the biomarkers because of their high surface area. When the metal ions participate in the oxidation of the biomarkers, electron transfer occurs from the biomarker to the metal ions, which can be collected through the $TiO_2$ nanotubes. The nanotube structure has enhanced charge transport properties and can conduct the electrons with minimal losses.

In order to verify candidate metal cations identified for binding the different biomarkers, cyclic voltammetry studies can be carried out in electrolytes consisting of different metal cations with different concentrations. For example this method was previously carried out in Co(II), Zn(II), and Cr(III) solutions for detection of methyl nicotinate and methyl p-anisate. It was observed that Co(II) showed better results than other metal cations in sensing methyl nicotinate. FIG. 6 shows preliminary cyclic voltammetry results conducted in different concentrations of Co(II) with and without addition of different concentrations of methyl nicotinate. The reduction and oxidation waves of pure Co(II) solution are larger than the solutions containing methyl nicotinate. These results indicate that when nicotinate forms a complex with Co(II), fewer cobalt ions participate in the reduction reaction which also decreases the oxidation curve. When the concentration of cobalt ions is 10 mM, two oxidation peaks are noted. The first peak at less positive potentials could be attributed to the reaction:

$$Co \rightarrow Co^{2+} 2e- \; E^{O} = -0.227 + 0.0295 \log [Co2+] \; V(SHE) \quad (5)$$

The second anodic peak at more positive potentials could be attributed to the reaction:

$$Co + H_2O \rightarrow CoO + 2H^{+b} \; {}^{2}e- \; E^{O} = 0.095 - 0.059 \; pH \; V(SHE) \quad (6)$$

At very low concentrations of Co(II), reaction (5) is not significant because of almost complete complex formation. The reduction in current densities of cathodic and anodic waves of the cyclic voltammetry can be correlated with the concentrations of the nicotinate. Based on modeling in Example 4 and verification using cyclic voltammetry studies, the type of metal cations and their concentration can be selected for binding different biomarkers.

Example 6—Preparation of Self-Ordered $TiO_2$ Nanotubes

The 3D $TiO_2$ nanotube array format creates a sensor with extremely high surface area within a small amount of space. The tubular morphology allows more potential areas to be functionalized with elements that can bind volatile biomarkers, thus increasing the sensitivity. In addition, the $TiO_2$ nanotubes have excellent charge transport properties after annealing which makes them suitable for detecting binding events that occur on the nanotube surface. FIG. 1 shows an image of an array fabricated using self-ordered TiO2 nanotubes.

Among the various available methods for preparing nanotubular templates, electrochemical anodization is considered simple, inexpensive, and easily scalable to large area synthesis. A well-established methodology to fabricate self-ordered and vertically oriented $TiO_2$ nanotubular templates using an ultrasound assisted anodization process has been developed. The ultrasonication results in better ordering of the nanotubes.

Templates of $TiO_2$ nanotubular oxide arrays can be formed by anodization of Ti foils (0.1 mm thick) in an electrolytic solution consisting of 0.5 wt % $NH_4F$+5 vol % $H_2O$ in ethylene glycol under an ultrasonically agitated condition using an ultrasonic bath (100 W, 42 KHZ, Branson 2510R-MT). A two-electrode configuration can be used for anodization. A flag shaped platinum (Pt) electrode can serve as a cathode. The anodization can be carried out by varying the applied potential from 20 to 60 V using a rectifier (Agilent, E3640A). Varying the anodization potential can control the diameter of the tubes, and changing the anodization time can vary the length of the tubes. The as-anodized $TiO_2$ templates can be annealed in oxygen at 500° C. for 6 h to increase their electrical resistance. $TiO_2$ nanotubes can have very high electrical resistance so that when the nanotubes are biased appropriately and binding events occur between the functionalized nanotube and volatile biomarker, a current change is detected. The nanotubes can form ordered arrays of vertically oriented and free standing $TiO_2$ oxide nanotubes. Dimensions can vary as previously discussed but in this example typically exhibit diameters in the range of 100-200 nm, length in the range of 1-3 μm, and wall thickness in the range of 5-10 nm.

Example 7—Functionalization of $TiO_2$ Nanotubes

Functionalization of the nanotubes is useful for the proposed methodology for diagnosing TB. The functionalization technique applied can enhance stability of the sensors (shelf-life of 6 months). In some cases, the functionalized nanotube array can contain a minimum of 3 wt % of the metal ion embedded in the nanotube array.

Functionalization of the nanotube array can be carried out using metal ion exchange methods known in the art. Exchanging metal ions (Co, Zn, Cr, etc.) onto the $TiO_2$ nanotube surface is made possible by the presence of large numbers of hydroxyl (Ti—OH) groups at the surface, which has been confirmed by XPS analysis. Previous results reveal that almost 40% of the surface is covered by hydroxyl groups which are Brönsted acid sites and are known to be exchangeable sites. The exchange process of the surface hydroxyl proton with candidate metal ions is shown in the equation below (M=Zn, Co, Cr, and other candidate ions):

$$2Ti-OH + M^{2+} = 2Ti-O-M + 2H^+ \quad (7)$$

For example when functionalizing $TiO_2$ nanotubes with Co, the following method is used:
1) Dehydrate the $TiO_2$-NT by heating at 100° C.
2) Soak the nanotubes in a solution of Cobalt (II) Chloride (0.5 wt % of Cobalt (II) Chloride ($CoCl_2$, 99.7%, Alfa Aesar, USA) dissolved in 100 ml of ethanol, and reacted in ultrasonication bath for 30 minutes.
3) Rinse the sample and dry in a vacuum oven at 100° C.

This method results in functionalization of the metal on the $TiO_2$ nanotubes and has been successfully demonstrated using Zn and Co. This method can be used with other metals identified as binders for TB volatile biomarkers. To verify the presence of the inorganic element, EDS and XPS analysis can be done which can yield the elemental composition of the sample and the amount present.

An exemplary method for preparing an array of $TiO_2$ nanotubes functionalized with cobalt(II) ions includes the steps of anodization, annealing, and functionalization. First, a potential of 30 V is applied for 60 minutes to a titanium anode and a platinum cathode in a solution of 97% ethylene glycol and 0.5 wt % $NH_4F$ in water. Then, the nanotubes are annealed under oxygen by heating the nanotubes to 500° C. and holding at that temperature for 2 hours. Finally, the nanotubes are functionalized with cobalt by soaking the nanotubes in an ultrasonic bath of 0.5 wt % $CoCl_2$ in EtOH.

Example 8—Investigation of Performance of Functionalized Nanotube Arrays for Detection of Candidate Gaseous Volatile Biomarkers In order to achieve rapid detection of the candidate TB biomarkers, the operating conditions of the sensor can be optimized in order to achieve rapid and clear detection. Under optimal conditions, the sensor response can be on the order of seconds.

In order to determine the appropriate biasing conditions for detection of the volatile biomarker, each substrate functionalized with a different element can be characterized for each of the volatile markers to determine at what point the sensor is most sensitive. To achieve this, a voltage sweep from −5V to 5V (using a Gamry Potentiostat) can be conducted on each sensor with associated volatile biomarker to see where the maximum change in current occurs when the volatile biomarker is introduced to the nanotube sensor array. Once this has been achieved, the sensor can be tested to quantify its performance at different concentrations of the volatile biomarker. These concentrations can be from 100 ppm down to 1 ppb. The goal is to optimize the sensor for detection of levels at the 1 pbb or lower which should be sufficient to not only detect low levels of biomarkers given off by the mycobacterium, but also detect the biomarkers at the latent stage of TB as only small numbers of mycobacterium are required to give off the biomarker.

Example 9—Characterizing the Selectivity and Sensitivity of the Sensor for the TB Volatile Biomarkers in a Complex Mixture of Gases (i.e. in the Presence of Other Volatiles)

To characterize the sensor performance in the presence of other VOCs commonly found in human breath. The selectivity and sensitivity can be characterized and optimized to handle a real world sample.

The breath of humans contains many VOCs that have been characterized. The major VOCs in breath of healthy individuals are isoprene (12-580 ppb), acetone (1.2-1,880 ppb), ethanol (13-1,000 ppb), and methanol (160-2000 ppb). Minor components are acetaldehyde (3-7 ppb) and hexanal (9-13 ppb). The sensor can be tested in the presence of these VOCs and TB volatile biomarkers to determine its selectivity.

An environmental chamber (Vacuum Atmosphere Corporation) with precise control over temperature, pressure, humidity and gas flow can be used to create an environment where common VOCs are present with the target volatile biomarkers. Mixtures of the "background VOCs" can be set to concentrations in the ppb range using levels described previously. The concentration of each volatile biomarker can be varied separately (meaning only 1 volatile biomarker can be present per test) starting at 1 ppb and increasing the concentration to 1000 ppb. Then the sensor response can be examined. Experiments can then be repeated for mixtures of samples that include all four volatile biomarkers. The results can be verified using Mass Spectrometry as the standard for the test. This can be used to determine the sensitivity and selectivity of the sensor. The results of the sensor can be compared to the results of Mass Spectrometry and false positives, false negatives, true positives, and true negatives can be used to determine the sensitivity and selectivity.

Volatile biomarkers at low levels can be concentrated. One way is to recirculate the air around the sensor to allow more molecules to bind to the sensor. Another method can be to use solid phase extraction fibers to collect the gas and then elute the gas from the fibers near the sensor by using heat. Either of these types of methods can be integrated into a microchannel platform. In addition, if cross reactivity between binding elements on the sensor exists, and then modifying the bias voltage of the sensor can be investigated to "tune" the sensor response so that the sensor detects the desired volatile biomarker. Filtering mechanisms to remove unwanted VOCs for processing the breath can also be used to enhance sensor performance.

Example 10—Characterizing the Sensor in Response to Environmental Factors Such as Gas Flow Rate, Temperature and Humidity In order to achieve a reliable sensor that is capable of working in environments all over the world, it can be tested and characterized to determine under what condition the sensor operates and fails.

Preliminary results indicated that the effect of moisture was minimal when compared to signals from methyl nicotinate and methyl p-anisate. However quantitative data is needed to understand effects of humidity, temperature, and gas flow. An environmental chamber with precise control over these parameters can be used. The sensor can be placed in the chamber and exposed to each volatile biomarker separately. During each experiment the temperature can be changed by increments from −10° C. to 50° (just beyond the range of temperatures the sensor is expected to operate in). A similar experiment can be performed for humidity going from 0-100% in increments 5%. The rate of gas flow over the sensor could have adverse effects (causing noise in the signal) and this can be tested by changing the volumetric flow rate from 1 cubic foot/min (CFM) (1.7 cubic meters per hour) to 200 CFM (340 cubic meters per hour) in increments of 10 CFM (17 cubic meters per hour). The quantification of these parameters can allow for sensor optimization and define packaging schemes for implementing the sensor.

Example 11—Developing a Prototype for Packaging the Sensor into a Microchannel Platform for Processing of Air Samples as they are Delivered to the Sensor The $TiO_2$ sensor can be packaged into a portable microchannel network that handles/processes the incoming breath and delivers it to the sensor. Sensor packaging and integration into instrumentation is an aspect of this project. Packaging of the sensor can require knowledge from the above examples to help design components to be integrated in to the channel network for processing of the air such as filters, gas concentrators, and electrode pads to interface with the associated instrumentation. The packaging for the sensor part can also be disposable. However the sensors can be designed to be recyclable which not only reduce costs for subsequent sensors, but also reduce the accumulation and improper disposal of medical waste that exists in low resource countries.

Design and integration of the sensor into a microchannel can be done using soft lithography and 3D printing rapid prototyping techniques to develop various prototype designs. The packaging with integrated electrodes can be designed to interface with a portable potentiostat that can be run from a netbook, a smartphone or other mobile device for testing in the field.

Example 12—Copper Functionalized $TiO_2$ Nanotubes for Glutathione Detection

A 10 mm×10 mm square of titanium foil was cut, polished, and rinsed in isopropanol in ultrasonic bath for 5 minutes. Electrolyte for anodization was prepared with 0.5 w/v % of ammonium fluoride ($NH_4F$, Alfa Aesar, USA) dissolved in 3% DI water in ethylene glycol (EG, $C_2H_6O_2$, Alfa Aesar, USA). Platinum coil served as a cathode and titanium foil served as an anode in the EG solution applying 30 volts direct current (DC) for 1 h. Nanotube fabricated titanium samples were rinsed in deionized water for 5 seconds in an ultrasonic bath then dried in a 110° C. chamber for at least 1 day. Samples were annealed under an oxygen rich atmosphere to crystalize the anatase structure from amorphous $TiO_2$ at 500° C. for 2 h.

For metal functionalization, anatase nanotube samples were dipped in three different copper salt solutions that were prepared using 0.24 g of $CuSO_4$, 0.28 g of $Cu(NO_3)_2$, and 0.2 g of $CuCl_2$ in 50 ml of ethanol. These samples in solution were incubated in an ultrasonic bath for 30 minutes. Samples were rinsed in DI water with 3 seconds of ultrasonication then dried in a 110° C. chamber for 1 day.

Figure 7:
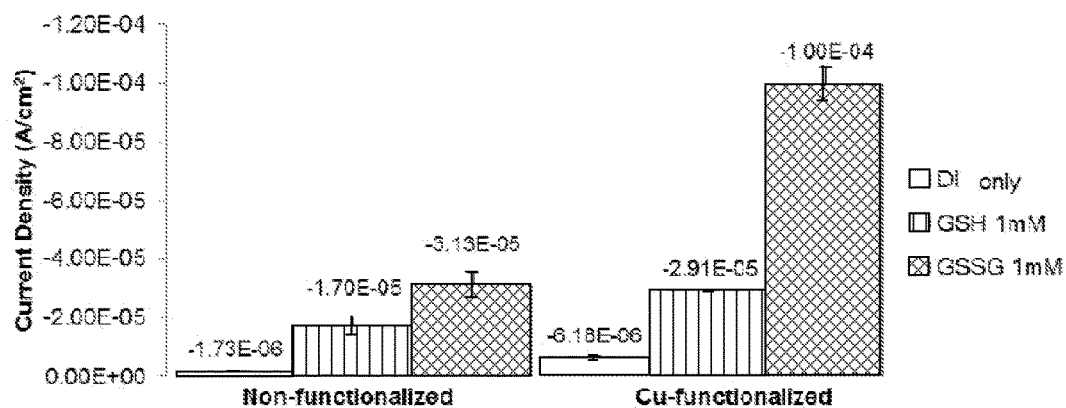
FIG. 7 is a graph of CV measurements of GSH and GSSG for copper functionalized titanium oxide nanotubes.

In FIG. 7, current density values at −300 mV of CV are compared. The current densities were −17 $\mu A/cm^2$ and −31.3 $\mu A/cm^2$ for GSH and GSSG with non-functionalized $TiO_2$-NTs and −29.1 $\mu A/cm^2$ and −100 $\mu A/cm^2$ for GSH and GSSG with Cu-functionalized $TiO_2$-NTs. The ratio of measured current densities of GSSG/GSH from non-functionalized $TiO_2$-NTs was 1.87. Cu-functionalized $TiO_2$-NTs showed higher signal than non-functionalized nanotubes, with a GSSG/GSH ratio from of 3.43, which is 1.83 times larger than for non-functionalized $TiO_2$-NTs. This indicates the selectivity of copper for glutathione.

It has been known that a carboxyl group at the gamma-glutamate residue of GSH is the binding site of copper, and thus it is expected that the ratio of GSSG/GSH is about 2. To put it another way, GSSG should show about 2 times higher current signal than GSH for copper in solution. Also, other publications that have shown the ratio of GSSG/GSH to be 2 have tested binding affinity through dissolved metal and dissolved GSH in the solution state. However, we use the immobilized copper metal for the dissolved glutathione solution. This difference might cause an unexpected GSSG/GSH ratio of 3, instead of 2.

Figure 8:
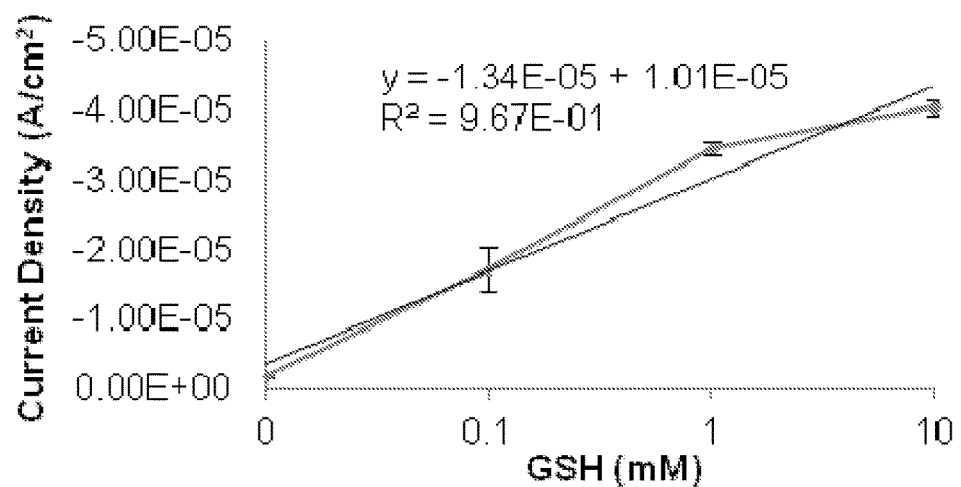
FIG. 8 is a plot of current density versus concentration of GSH for Cu—TiO$_2$-NTs. Reference will now be made to the exemplary embodiments illustrated, and specific language will be used herein to describe the same. It will nevertheless be understood that no limitation of the scope of the invention is thereby intended.

The current at −0.3 V of CV tests are proportional to logarithmic concentration of GSH. The GSH binding to Cu—$TiO_2$-NTs was tested in a well stirred GSH solution for 30 seconds, and the signal strength for each GSH concentration was plotted on a logarithmic scale of GSH concentration (X-axis) as shown in FIG. 8. The trendline of plot for 0-10 mM of GSH range shows slope of −1.34E-05 with 0.967 of $R^2$. It represents that the strength of electrical potential is the reason of binding, and the signal is well linearized until 10 mM concentration where is the normal concentration range of glutathione molecules in body fluid.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

The invention claimed is:

1. A sensor for detecting a volatile organic compound, comprising:
   a nanotube array including a plurality of functionalized metal oxide nanotubes, the metal oxide nanotubes being formed of a metal oxide and having at least one of an interior and exterior surface capable of binding with the volatile organic compound, said surface being functionalized with at least one metal ion selected from the group consisting of $Fe^{2+}$, $Pb^{2+}$, $Fe^{3+}$, $Cr^{3+}$, $Mn^{3+}$, $Mn^{4+}$, $As^{4+}$, $Pt^{4+}$, $Pd^{2+}$, $Pd^{4+}$, and combinations thereof;
   a power source configured to apply a voltage to the nanotube array; and
   a current sensor configured to monitor and detect changes in a response current which varies upon binding with the volatile organic compound.

2. The sensor of claim 1, wherein the metal oxide of the metal oxide nanotubes is selected from the group consisting of titanium dioxide, iron oxide, iridium oxide, tantalum oxide, zinc oxide, aluminum oxide, and combinations thereof.

3. The sensor of claim 1, wherein the power source is configured to apply a voltage of about −0.2 V to about −0.8 V.

4. The sensor of claim 1, further comprising a sample intake configured to direct flow of a sample gas over the nanotube array.

5. The sensor of claim 1, wherein the volatile organic compound is a biomarker for a physiological condition or disease.

6. The sensor of claim 5, wherein the biomarker is selected from the group consisting of methyl phenylacetate, methyl p-anistate, methyl nicotinate, o-phenylanisole, lactic acid, reduced or oxidized glutathione, uric acid, urease, and combinations thereof.

7. The sensor of claim 5, wherein the physiological condition or disease is selected from the group consisting of tuberculosis, breast cancer, lung cancer, heart disease, diabetes, preeclampsia, oxidative stress, and combinations thereof.

8. The sensor of claim 1, wherein the sensor is reusable following exposure of the functionalized nanotubes to ultraviolet light.

9. A functionalized nanotube array, comprising:
a plurality of metal oxide nanotubes, the metal oxide nanotubes formed of a metal oxide and having an interior or exterior surface that is functionalized with at least one metal ion selected from the group consisting of $Fe^{2+}$, $Pb^{2+}$, $Fe^{3+}$, $Cr^{3+}$, $Mn^{3+}$, $Mn^{4+}$, $As^{4+}$, $Pt^{4+}$, $Pd^{2+}$, $Pd^{4+}$ and combinations thereof.

10. The nanotube array of claim 9, wherein the metal oxide is selected from the group consisting of titanium oxide, iron oxide, iridium oxide, tantalum oxide, zinc oxide, aluminum oxide, and combinations thereof.

11. A method of detecting a volatile organic biomarker, comprising:
applying a voltage across a functionalized nanotube array, the functionalized nanotube array including metal oxide nanotubes being formed of a metal oxide and having at least one of an interior and exterior surface capable of binding with the volatile organic biomarker, and that is functionalized with at least one metal ion;
measuring a current passing over the functionalized nanotube array;
flowing a gas over a functionalized nanotube array such that the volatile organic biomarker can bind with the at least one metal ion of the metal oxide nanotubes;
monitoring the current for changes; and
identifying the volatile organic biomarker found in the gas based on the changes in current.

12. The method of claim 11, wherein the metal oxide of the metal oxide nanotubes is selected from the group consisting of $TiO_2$, iron oxide, iridium oxide, tantalum oxide, zinc oxide, aluminum oxide, and combinations thereof.

13. The method of claim 11, wherein the at least one metal ion is selected from the group consisting of $Cu^{1+}$, $Li^{1+}$, $Fe^{2+}$, $Ni^{2+}$, $Cu^{2+}$, $Co^{2+}$, $Pb^{2+}$, $Fe^{3+}$, $Co^{3+}$, $Cr^{3+}$, $Mn^{3+}$, $Ni^{3+}$, $Sc^{3+}$, $Sb^{3+}$, $Ni^{4+}$, $Mn^{4+}$, $Ti^{4+}$, $As^{4+}$, $Sb^{4+}$, $Pt^{4+}$, $Au^{1+}$, $Zn^{2+}$, $Pd^{2+}$, $Pd^{4+}$, $Ag^{1+}$, and combinations thereof.

14. The method of claim 11, wherein the volatile organic biomarker is selected from the group consisting of methyl phenylacetate, methyl p-anistate, methyl nicotinate, o-phenylanisole, lactic acid, reduced or oxidized glutathione, uric acid, urease, and combinations thereof.

15. The method of claim 11, wherein the gas is expelled breath from a human subject.

16. The method of claim 15, further comprising diagnosing the human subject with a physiological condition or disease based on the identifying of the volatile organic biomarker.

17. The method of claim 11, further comprising releasing volatile organic biomarker bound to the metal ions of the metal oxide nanotubes by exposing the metal oxide nanotubes to ultraviolet light.

18. The method of claim 11, wherein the at least one metal ion is selected from the group consisting of $Co^{2+}$, $Co^{3+}$, $Ni^{3+}$, $Ni^{4+}$, $Ag^{1+}$, and combinations thereof.

19. The method of claim 11, wherein the at least one metal ion is at least one of $Co^{2+}$ or $Co^{3+}$.

20. The method of claim 11, wherein the at least one metal ion is at least one of $Ni^{3+}$ or $Ni^{4+}$.

* * * * *